United States Patent [19]

Butterfield

[11] Patent Number: 5,423,743
[45] Date of Patent: Jun. 13, 1995

[54] CANNULA POSITION DETECTION

[75] Inventor: Robert D. Butterfield, Poway, Calif.

[73] Assignee: IVAC Corporation, San Diego, Calif.

[21] Appl. No.: 123,327

[22] Filed: Sep. 17, 1993

[51] Int. Cl.$^6$ .................................................. A61M 31/00
[52] U.S. Cl. ...................................... 604/50; 604/67; 128/DIG. 13
[58] Field of Search .............. 128/DIG. 12, DIG. 13; 604/65–67, 50, 118, 244, 245, 49, 50

[56] References Cited

U.S. PATENT DOCUMENTS

| | | | |
|---|---|---|---|
| 4,530,696 | 7/1985 | Bisera et al | 604/253 |
| 4,648,869 | 3/1987 | Bobo, Jr. | 604/49 |
| 4,710,163 | 12/1987 | Butterfield | 604/65 |
| 4,743,228 | 5/1988 | Butterfield | 604/50 |
| 4,816,019 | 3/1989 | Kamen | 604/65 |
| 4,846,792 | 6/1989 | Bobo, Jr. et al. | 604/50 |
| 4,959,050 | 9/1990 | Bobo, Jr. | 604/49 |
| 5,026,348 | 6/1991 | Venegas | 604/122 |
| 5,087,245 | 2/1992 | Doan | 604/67 |

OTHER PUBLICATIONS

T. S. Harris and W. W. von Maltzahn, "Infusion Line Model for the Detection of Infiltration, Extravasation, and other Fluid Flow Faults," *IEEE Transactions On Biomedical Engineering*, vol. 40, No. 2, Feb. 1993, pp. 154–162.

*Primary Examiner*—C. Fred Rosenbaum
*Assistant Examiner*—Adam J. Cermak
*Attorney, Agent, or Firm*—Fulwider, Patton, Lee & Utecht

[57] ABSTRACT

Bidirectional flow patterns are induced in a fluid supply line and the reverse flow resistance and the forward flow resistance are measured and compared. A measure of the resistance to flow is made by normalizing a sum of the entire pressure response about a pressure baseline according to the volume of fluid in the bidirectional flow pattern. In the event that the cannula is positioned near or against the vessel wall, the resulting relatively large negative pressure response can indicate the positional irregularity. In one embodiment, a time period of zero flow is included between the positive and negative flow volumes to permit the system to stabilize.

41 Claims, 10 Drawing Sheets

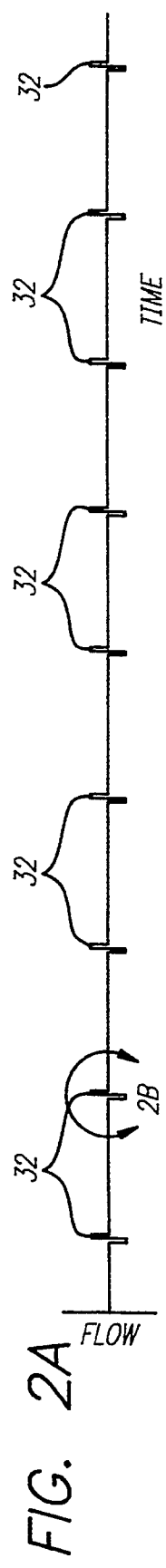
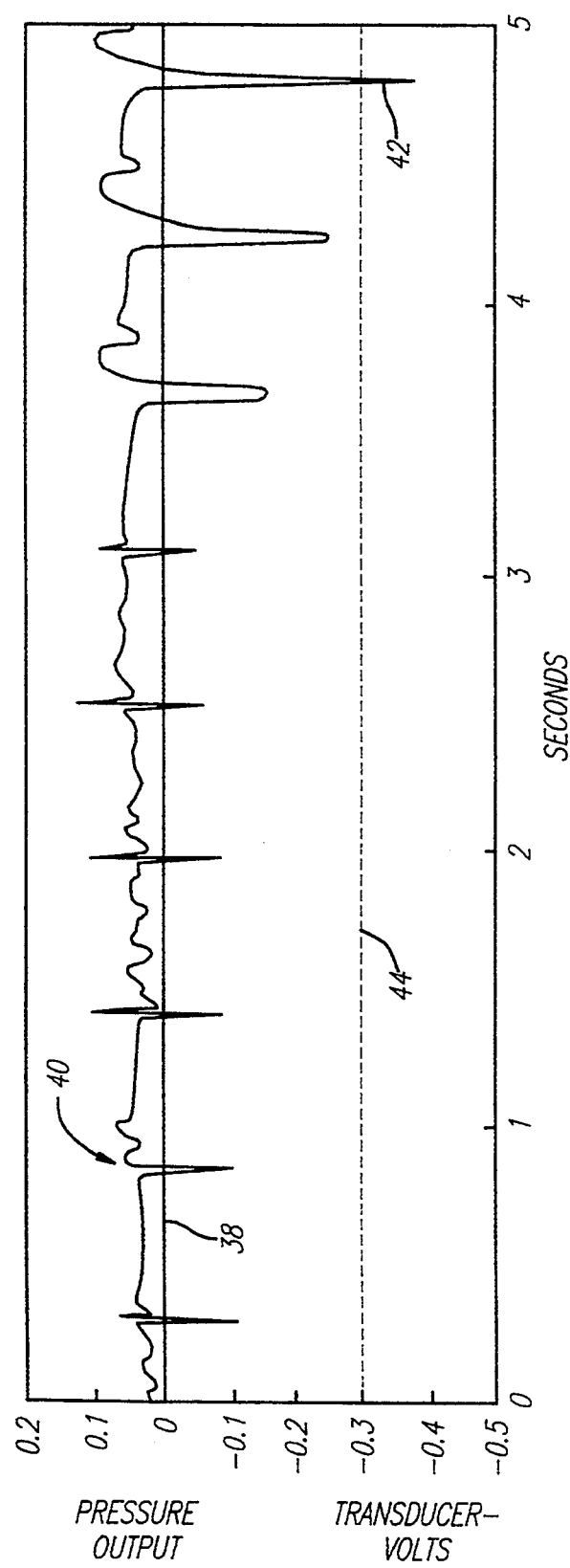
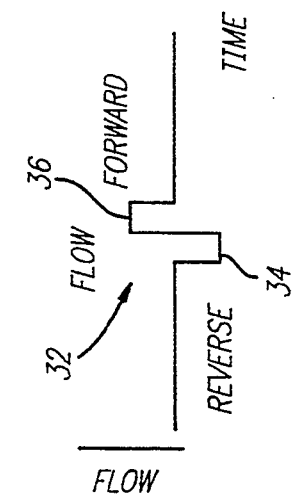
FIG. 2A
FIG. 2B
FIG. 2C

FIG. 3A(1)
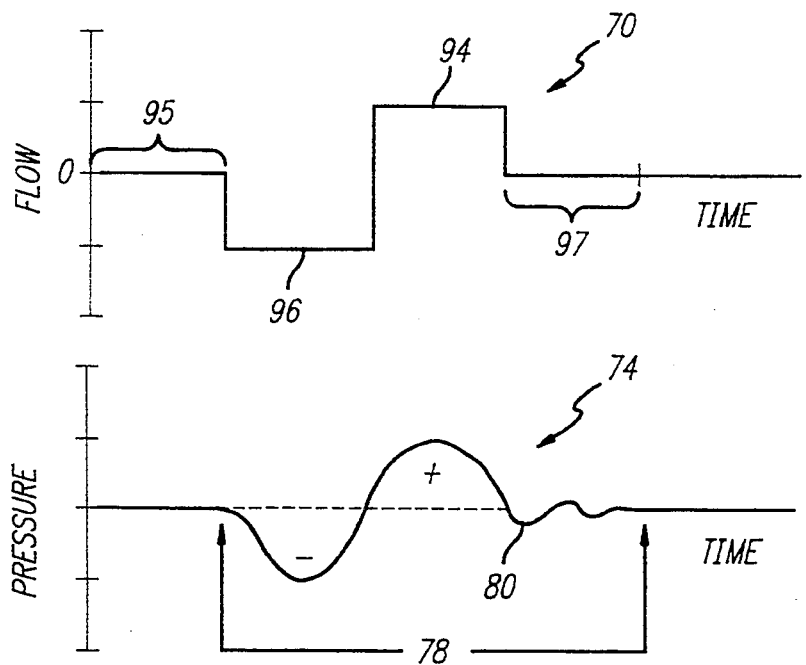
FIG. 3A(2)
FIG. 3B(1)
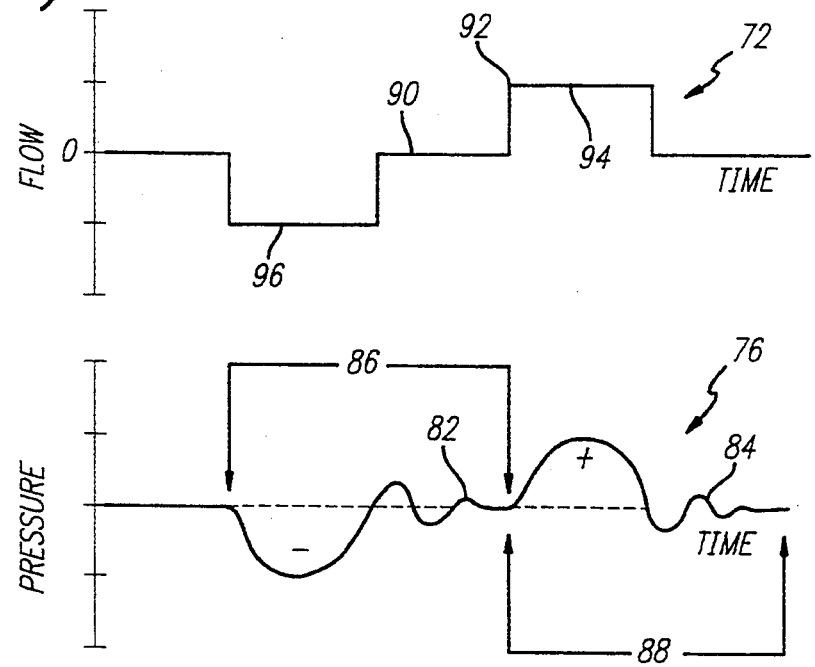
FIG. 3B(2)

CANNULA POSITION DETECTION

BACKGROUND

The invention relates generally to monitoring the delivery of fluid through a fluid delivery system, and more particularly, to detecting the position of a cannula used in delivering fluid to a patient's blood vessel.

Fluid delivery systems for intravenously infusing fluid to a patient typically include a supply of the IV fluid, an infusion needle or cannula, an IV administration set connecting the fluid supply to the cannula, and a positive displacement infusion pump. The cannula is mounted at the distal end of the flexible tubing of the IV administration set for insertion into a patient's blood vessel to deliver the fluid infusate to the patient. One commonly used infusion pump is a peristaltic type having several rollers, cams or cam-actuated fingers which sequentially occlude portions of the flexible tubing along a pumping zone to create a moving zone of occlusion. The peristaltic action forces the IV fluid through the tubing of the administration set to the cannula and into the patient.

During infusion, conditions such as phlebitis and/or infiltration may develop if the cannula is allowed to press against the vessel wall continuously. Phlebitis is the inflammation of the vessel wall due to the action of the undiluted infusate directly contacting the vessel wall. Infiltration is a condition in which infused fluid finds its way into extravascular tissues rather than being released solely into the blood stream. When this occurs, fluid may be infused into the interstitial spaces between layers of tissues. Not only is the patient deprived of proper intravenous drug administration, but the patient is further subjected to the possible toxic or caustic effects associated with the infused fluids directly contacting body tissue.

A commonly used manual clinical technique for evaluating catheter patency and for detecting infiltration involves an attempt to aspirate a small volume of blood from the cannula. This is implemented either by attachment of a syringe to an injection site in the IV line or by use of a device commonly referred to as a "flashball" which is a component of the IV administration set itself. After introduction of the cannula into the blood vessel, a small volume of IV fluid is first infused by squeezing the ball, and then releasing it. If blood is aspirated into the cannula and the IV set, then patency of the cannula is assumed. Aspirated blood must be reinfused with a rapid flush in each method.

However, the manual methods have several disadvantages including: risk of contamination; non-continuous monitoring; interruption of therapy, which is a particularly acute disadvantage when high potency, rapid acting drugs are infused; the potential for clot dislodgement; and potential for vessel damage and inconsistent technique and judgement criteria.

Methods have been developed for detecting the existence of an extravascular infiltration; however, such methods including the above-described manual method are generally directed at detecting an infiltration after it has occurred. These methods are typically not sensitive to cannula positional irregularities where the cannula remains in the patient's vessel but has moved into a position from which it may eventually progress to an infiltration. For example, a cannula that is inside the vessel but which has gradually moved into a position such that its output port is in contact with the vessel wall or at least directs the IV solution directly against the vessel wall may result in vessel wall damage leading eventually to phlebitis and/or infiltration as the vessel wall intima is irritated. Should this position of the cannula be detected early enough, infiltration may be avoided. Hence, those skilled in the art have recognized that it would be beneficial to detect a cannula which has moved against the vessel wall before substantial damage to that wall has occurred.

Other systems have been devised for the detection of abnormalities in an intravascular infusion system by use of simple monitoring of the infusion pressure. A high or increasing pressure may be interpreted as either an infiltration or an occlusion. A low pressure may be interpreted as an unobstructed line or a line that has completely withdrawn from the vessel. However, the pressure developed at a given flow rate in an intravascular system depends on many factors, such as motion and position of the patient, respiration, arterial or venous blood pressure of the patient, and the size and position of the cannula used. Such factors create a considerable uncertainty in the measurement of pressure, and may cause difficulty in interpretation of pressure readings.

Observation of the pressure response of a fluid delivery system to a flow pattern to determine when the pressure returns to a normal steady state equilibrium can give some information as to the effectiveness of fluid delivery. Application of fluid flow excitation volumes and the comparison of pressure responses of the system against a reference value are also known. However, the effectiveness of such techniques is lessened by patient movement, respiration, arterial or venous blood pressure, and other factors.

It has also been proposed in the art that infiltration can be detected by identifying a substantial lack of symmetry between the pressure response time to a positive fluid pulse and the pressure response time to a negative fluid pulse. In such a system, the pressure response to each pulse is monitored to determine the point in time that the pressure response reaches a predetermined reference pressure. The accuracy of such as system can be impacted by the existence of artifacts. For example, movement of the patient during the time that the pressure response is monitored can result in the pressure reaching the predetermined reference pressure prematurely, causing inaccuracy.

Hence, those skilled in the art have recognized a need for a cannula position detection system which can detect an undesirable cannula position prior to an infiltration and which can continuously monitor the position without interrupting therapy. Additionally, it has also been recognized that there is a need for a system that is relatively insensitive to patient movement and other factors which may affect the monitoring of the infusion. The present invention fulfills these needs and others.

SUMMARY OF THE INVENTION

Briefly and in general terms, the present invention relates to an apparatus and a method which monitor the pressure response of a patient fluid supply system in which a cannula is positioned in the patient's vascular system to a bidirectional fluid flow pattern to determine whether the resistance of the system during the flow volume in the upstream direction outweighs the resistance of the system during the flow volume in the downstream direction. An alarm is provided if the comparison result is outside a predetermined range. Based on the comparison of the resistance measurements, an undesirable cannula position can be determined.

In an aspect of the invention, a baseline pressure is determined from pressure measurements during a stopped flow condition and is considered in determining the resistances. The baseline pressure may be determined by first establishing a downstream fluid flow, stopping that flow before the bidirectional flow pattern is applied, monitoring the pressure during the period of stopped flow, and monitoring the fluid pressure again with flow stopped after the occurrence of the bidirectional flow pattern. The baseline pressure is determined from the periods of stopped flow. In a further aspect, the pressures occurring during the periods of stopped flow are averaged to result in the baseline pressure.

In another aspect, the position of a cannula inserted into the vascular system of a patient is determined, the cannula is coupled to the downstream end of a conduit that is connected at its upstream end to a reservoir of fluid. A baseline pressure based on the pressure in the conduit when no flow of fluid is occurring is established. A first predetermined quantity of fluid is moved towards the upstream end of the conduit and the pressure in the conduit during the movement of the predetermined quantity of fluid towards the upstream end is measured. A second predetermined quantity of fluid is moved towards the downstream end of the conduit and the pressure in the conduit during the movement is measured. The differences between the measured pressures and the baseline pressure are summed and are normalized by the respective quantity of fluid. The normalized sum is compared to a predetermined range and an alarm is provided if the normalized sum is outside the predetermined range.

In a more detailed aspect in accordance with the invention, resistance measurements are made during the application of a plurality of bidirectional flow patterns and the differentials between the respective resistance measurements are filtered to result in a filtered resistance differential. An alarm is provided only if the filtered resistance differential is outside the predetermined range. Filtering is performed in one aspect by averaging the resistance differential to result in the filtered resistance differential. In other aspects, filtering may also be accomplished by using a sliding average, a finite impulse response filter, an infinite impulse response filter, and a least squares fit.

In another aspect in accordance with the invention, an alarm is not provided unless one or more subsequent resistance differential measurements confirm that the resistance differential is outside the predetermined range.

In another aspect of the invention, the bidirectional flow pattern may include a delay between the upstream flow volume and the downstream flow volume to permit the pressure to stabilize between these volumes. In one embodiment of the invention, a pump is used which provides continuous occlusion of the conduit and the pressure measurements are taken at a point between the occlusion provided by the pump and the patient.

In yet another aspect of the invention, the resistances are determined by taking a numerical sum of the differences between the pressures resulting from the upstream and downstream flow volumes and the baseline pressure. The sum is normalized by dividing the sum by the aspiration and infusion volumes. In one case the aspiration and infusion volumes are equal but in another case, they are different. In the case where they are different, each summed pressure response to the respective flow volume is individually normalized before it is summed with the other.

In yet another aspect, the measure of the resistance differential is averaged over several such bidirectional flow pattern measurements to be relatively insensitive to patient motion or other artifacts affecting the system.

Other aspects and advantages of the invention will become apparent from the following detailed description and the accompanying drawings, which illustrate by way of example the features of the invention.

BRIEF DESCRIPTION OF THE DRAWINGS

FIG. 2A is a graphical representation of bidirectional fluid flow patterns introduced into the fluid delivery system in accordance with one aspect of the invention;

FIG. 2B is an enlarged view of one of the bidirectional fluid flow patterns of FIG. 2A;

FIG. 2C is a graphical representation of pressure responses to respective fluid flow volumes of FIG. 2A showing pressure responses representing normal cannula positioning and irregular cannula positioning;

FIG. 3A is a graphical representation of a bidirectional flow pattern and the output pressure response measured during the pattern;

FIG. 3B is a graphical representation of a bidirectional flow pattern with delay between the upstream and downstream flow volumes for pressure stabilization and file output pressure response measured during the pattern;

DETAILED DESCRIPTION OF THE PREFERRED EMBODIMENTS

Figure 1:
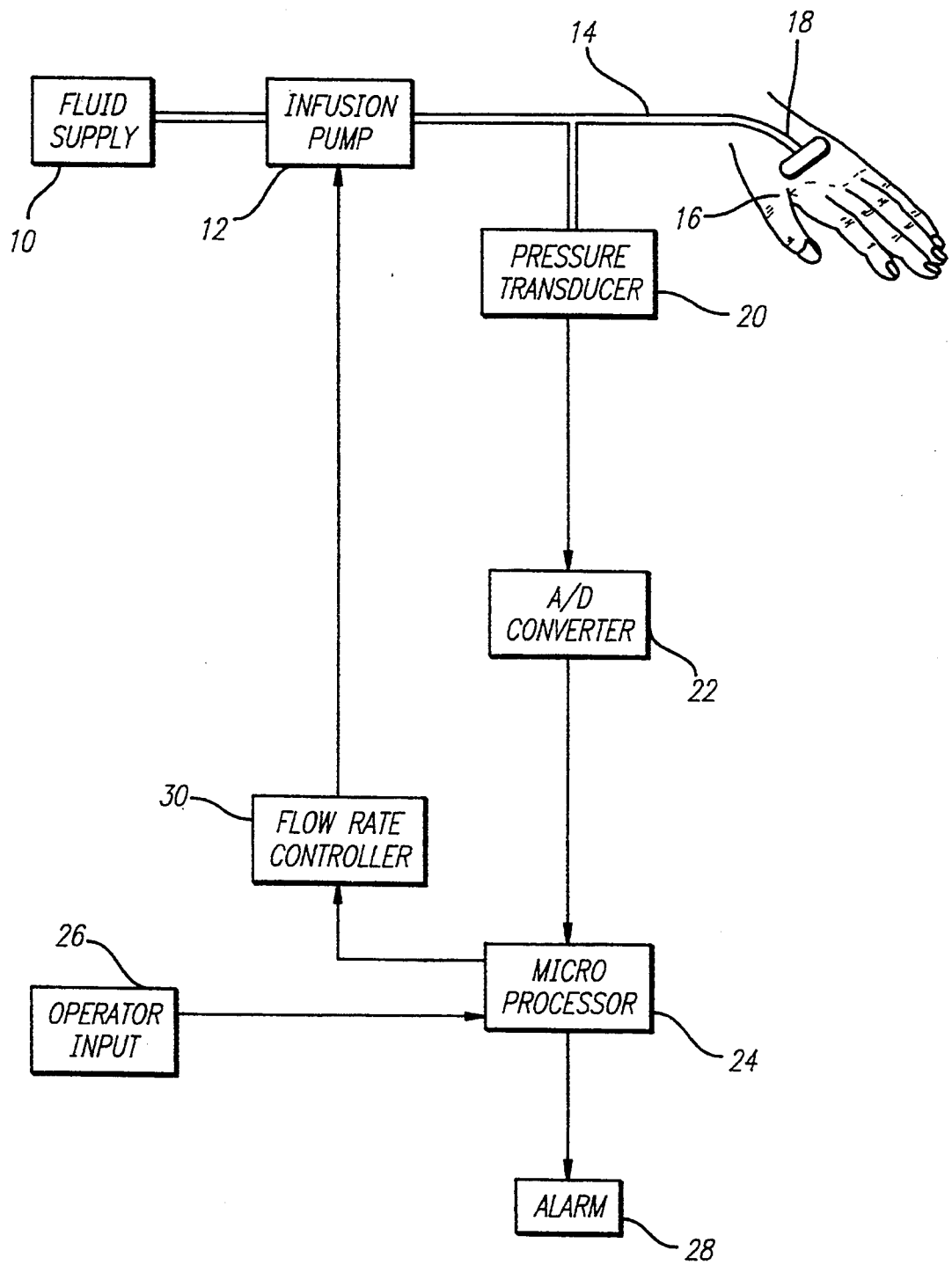
FIG. 1 is a schematic diagram of a fluid delivery monitoring system embodying features of the invention.

Returning now to the drawings with more particularity, wherein like reference numerals designate like or corresponding elements among the several views, there is shown in FIG. 1 an intravenous fluid administration system comprising a fluid supply 10, an infusion pump 12, an administration set comprising a fluid conduit 14, and a cannula 18 mounted at the end of the conduit and inserted in a blood vessel of a patient 16. A pressure transducer 20 is coupled to the conduit 14 and monitors the pressure existing in the conduit 14 between the infusion pump 12 and the patient's blood vessel and produces a signal representing the detected pressure.

In this embodiment the conduit comprises flexible tubing and the infusion pump is a linear peristaltic pump having a plurality of pumping fingers which sequentially occlude the conduit at all times. At least one pumping finger of the pump is at all times occluding the conduit. There is therefore no direct flow path between the fluid supply 10 and the patient 16.

An analog-to-digital converter 22 converts the analog signal from the pressure transducer 20 into digital signals which are transmitted to a microprocessor 24. The microprocessor 24 is preferably provided with an operator input unit 26, through which the operator may set the operational fluid flow rate and activate the pressure monitoring system. An alarm 28 is connected to the microprocessor for communicating certain system conditions to the operator. Additionally, a flow rate controller 30 controls the operation of the infusion pump 12 in response to microprocessor 24 signals. The use of an infusion pump as a flow control device is given here as an example. Other flow control devices may be used. Additionally, different types of infusion pumps may be used such as linear peristaltic, rotary peristaltic, piston type pumps and others.

Referring now to FIGS. 2A, 2B, and 2C, flow patterns in accordance with one aspect of the invention and resulting pressure responses are graphically illustrated. In FIG. 2A, a series of flow patterns 32 is provided, one of which is shown in more detail in FIG. 2B. These flow patterns 32 each comprise an upstream or reverse flow volume 34 followed by a downstream or forward flow volume 36.

Examples of pressure responses to each of these flow patterns 32 are shown in FIG. 2C which is aligned below FIG. 2A for convenience in comparison. Each flow pattern 32 in FIG. 2A has a respective pressure response shown below it in FIG. 2C. In FIG. 2C, a progression of pressure responses is presented showing pressure response curves for a cannula properly positioned in the patient's blood vessel at the left end of FIG. 2C and pressure response curves for an improperly positioned cannula at the right end of FIG. 2C. In FIGS. 2A and 2C, continuous pressure samples were taken at the rate of approximately 200 samples per second during repeated cycles of fluid withdrawal and reinfusion.

Pressure baseline 38 (FIG. 2C), which is at the level of 0 volts output from the pressure transducer, is used to illustrate the differences in the negative pressure transients during samples taken of a cannula positioned away from the vessel wall, shown generally at 40, and pressure transients during samples taken of a cannula positioned near a vessel wall, shown generally at 42. As is apparent, the negative pressure transients increase towards the right side of the figure. A threshold line 44 has been drawn in FIG. 2C to indicate the point of negative pressure at which an improperly positioned cannula may be suspected although as is described below in more detail, the resistance difference is taken into account to determine the existence of an improperly positioned cannula in accordance with one aspect of the invention.

Referring now to FIGS. 3A and 3B, a bidirectional flow pattern 70 and bidirectional flow pattern with delay 72 between the upstream and downstream volumes are shown respectively along with corresponding dynamic pressure responses 74 and 76. As illustrated, negative flow shown in the figure indicates upstream or reverse flow while positive flow indicated downstream or forward flow. The sum window 78 which defines the pressure response sampling period for the first bidirectional flow pattern 70 without delay is of a sufficient time period to encompass also the natural decay part 80 of the hydraulic pressure response. The sum window of the pressure response 76 resulting from the second bidirectional flow pattern 72 with delay between the upstream and downstream volumes encompasses both response periods 82 and 84 of both volumes of the bidirectional flow pattern. The sum window comprises two summation periods 86 and 88 that encompass the hydraulic pressure response to each flow volume. The first summation period 86 ends at the end of the delay period 90 and the second summation period 88 begins at the start 92 of the downstream flow volume 94 of the bidirectional flow pattern with delay 72. In this embodiment, the end of the delay period 90 and the start 92 of the downstream flow volume 94 coincide although other embodiments may impose a further delay before the start of the second volume of the bidirectional flow pattern 72.

The delay 90 in the second flow volume 72 permits the pressure response to the upstream volume 96 of the flow pattern 72 to be substantially decayed to baseline pressure before the downstream flow volume 94 is applied. It will be appreciated that the dynamic pressure response 76 resulting from the bidirectional flow pattern with delay 72 is useful to more clearly measure the dynamic pressure response during the upstream flow volume 96. Without the delay 90, part of the pressure response to the upstream flow volume 96 may be imbedded in the pressure response to the downstream flow volume 94 as is the case in FIG. 3A.

Preceding the upstream flow volume 96 and following the downstream flow volume 94 in FIG. 3A are non-flow periods 95 and 97 respectively. It is during these periods that the baseline pressure may be established as is described below in detail.

Figure 4:
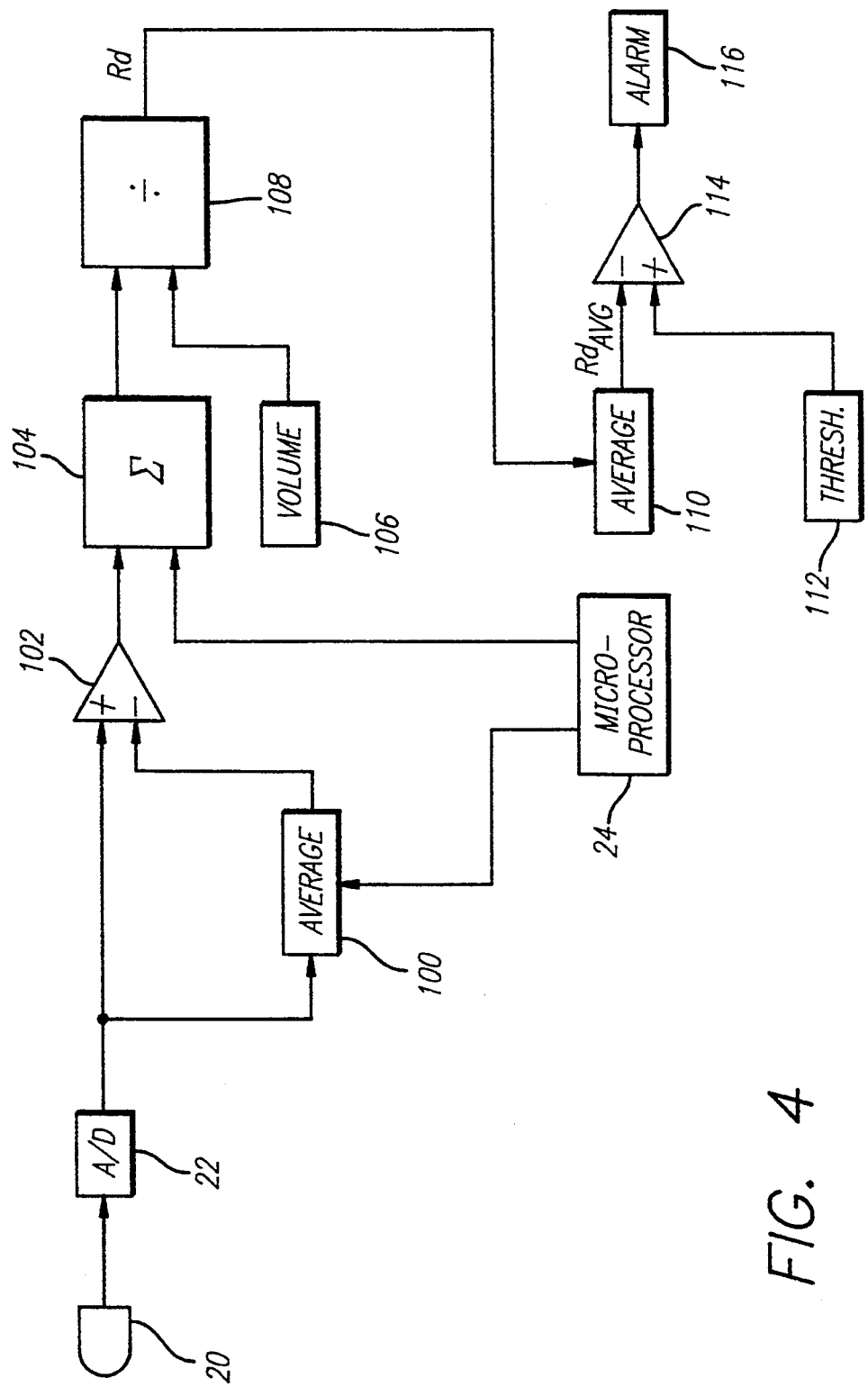
FIG. 4 is a schematic block diagram illustrating a system for determination of the resistance differential over a series of bidirectional flow patterns and for providing an alarm in the event that the resistance differential is more negative than a negative threshold.

Referring now to FIG. 4, a schematic block diagram is presented in which the pressure transducer 20 is sampled by the analog-to-digital (A/D) converter 22 at approximately 200 samples per second. In one embodiment, the microprocessor 24 commands the flow rate controller 30 (FIG. 1) to stop flow in the conduit both before and after a bidirectional flow pattern. The baseline sampler/averager 100 processes data from the A/D converter 22 before and after the bidirectional flow pattern to determine the pressure within the conduit 14 (FIG. 1) of the fluid administration system during these non-flow intervals. The microprocessor 24 averages those pressure samples and assigns the averaged result as the baseline pressure. The timing clock of the microprocessor 24 triggers the intervals for monitoring data to determine the pressure baseline and for the pressure response to bidirectional flow patterns.

During a bidirectional flow pattern, a numerical summation of .the relative balance between negative and positive halves of the resulting pressure response is made by summing the entire pressure about the baseline pressure established during the non-flow intervals before and after the bidirectional pattern. The numerical sum of the continuous sequence of individual pressure samples summed about the pressure baseline is normalized by the aspiration/reinfusion volume to result in a resistance difference measurement. This measure of the resistance differential can be expressed by the following equation:

$$R_d = R_{Fwd} - R_{Rev} = \sum_{n=0}^{N-1} \frac{[P(nT) - P_{baseline}] \times T}{Q}$$

where:

$R_d$ is the normalized resistance differential;

$R_{Fwd}$ is the downstream flow resistance in (mmHg-sec)/μL;

$R_{Rev}$ is the upstream flow resistance in (mmHg-sec)/μL;

N is the sample count required to include the pressure response;

T is the sampling interval period of the A/D convertor in seconds;

nT is the $n^{th}$ sample index at interval T seconds such that $P(nT)=P(t)|_{t=nT}$ where $0<n<N-1$;

P is the measured pressure;

Q is the aspiration/reinfusion volume in microliters (1LL); and $P_{baseline}$ is the average of pre-pattern and post-pattern non-flow interval pressures where the pre/post pressures may be time averaged values.

Now applying this formula to FIG. 4, data from the A/D convertor 22 is processed through a comparator 102 along with the measured baseline pressure from the averager 100. The result is provided to the numerical summer 104 which totals all the logic comparator 102 results multiplied by the sampling interval T provided by the microprocessor 24 during the bidirectional flow pattern period. The result, in the preferred embodiment, is a pressure-time numerical sum using the described mathematical method of integration by discrete summation. At the conclusion of the pressure response to the bidirectional flow pattern, the resistance differential ($R_d$) is calculated by dividing or normalizing the pressure-time sum from the summer 104 by the aspiration/reinfusion volume 106 in divider 108. In a further aspect, the $R_d$ is provided to a second averager 110 and is averaged with other such measurements to avoid false alarms caused by artifacts. An averaged $R_d$ ($R_d$ $_{Avg}$) is compared to a negative threshold value 112 in a comparator 114. If the result of the comparison is a positive value, an alarm 116 is preferably triggered.

Figure 5:
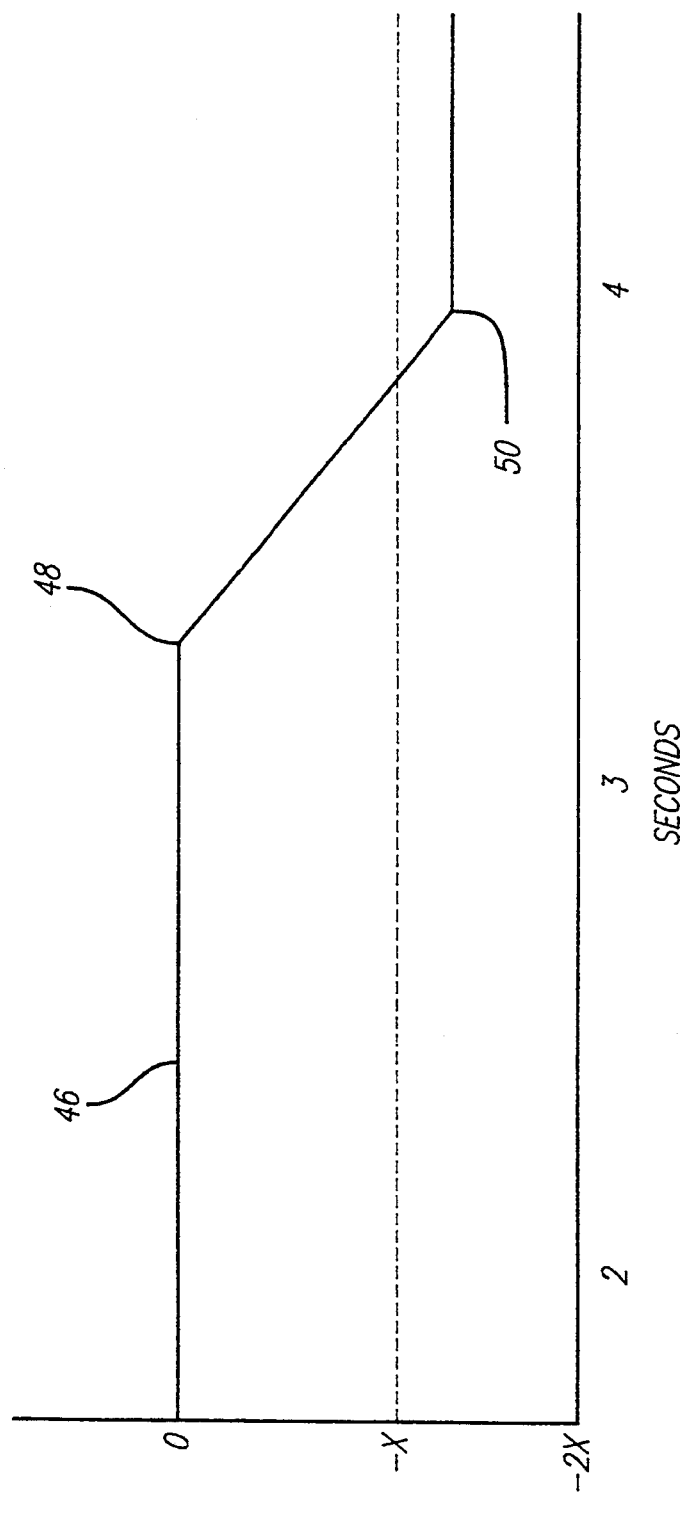
FIG. 5 is a graph of average resistance differential of the system of FIGS. 2A through 2C showing the differential associated with a properly positioned cannula and the differential associated with an improperly positioned cannula using a moving average computation.

A graph of average resistance differential is depicted in FIG. 5. Line 46 is representative of the average resistance over time and remains at level zero for approximately four seconds. At point 48, the resistance differential changes in a negative direction and proceeds to point 50 at level $-1\frac{1}{2}X$. Level $-X$ is a threshold for the average resistance differential at which an improperly positioned cannula is determined to exist. Upon crossing negative level $-X$, preferably an alarm is generated.

Figure 6:
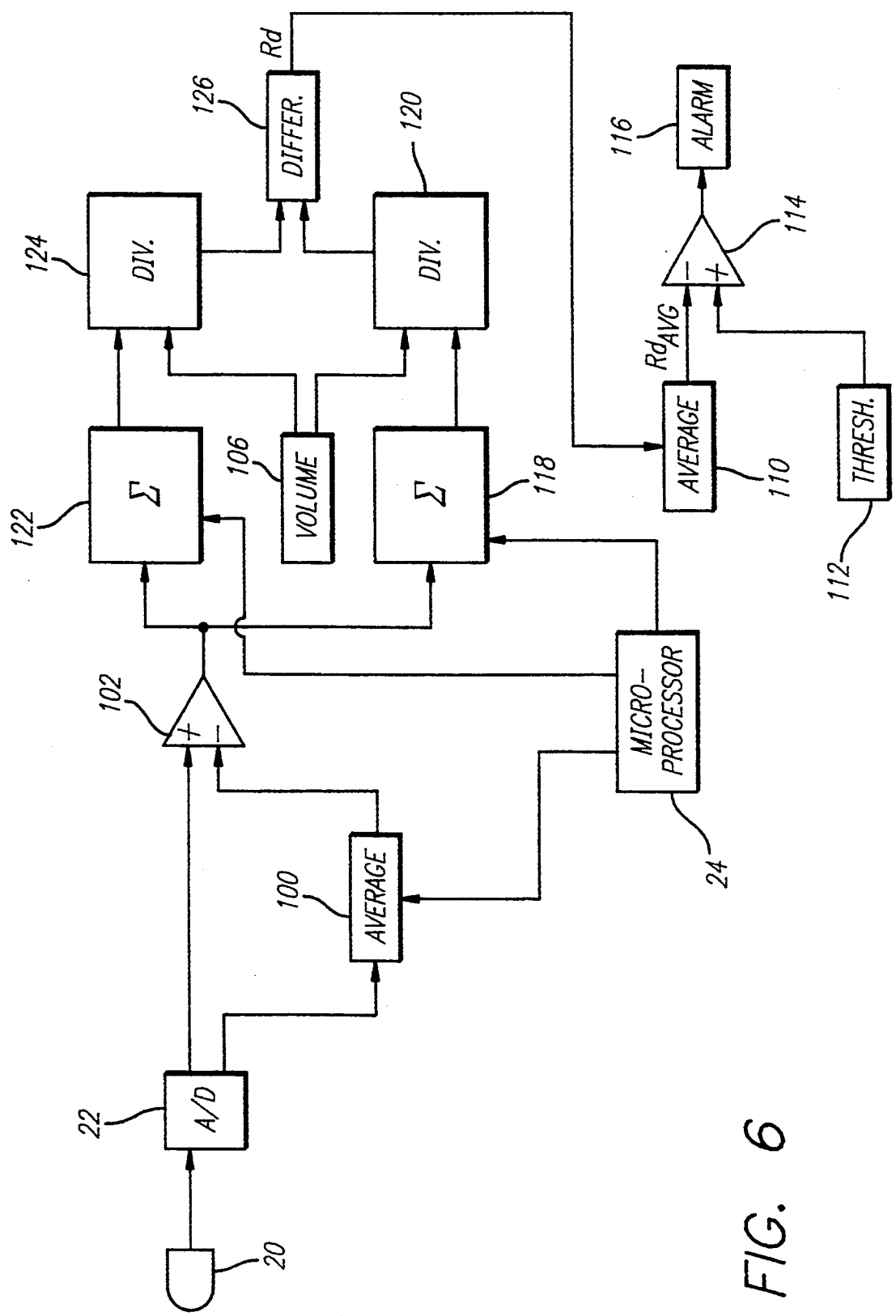
FIG. 6 is a schematic block diagram illustrating a system for determination of the upstream flow resistance and of the downstream flow resistance in response to bidirectional flow patterns, computation of the pressure-time sums, and comparison of the resistance difference to a negative threshold.

In the embodiment of FIG. 6, a processing system for the pressure response to a bidirectional flow pattern with delay is illustrated. The microprocessor 24 triggers the timing intervals to measure the baseline pressure by the first averager 100, the upstream flow pressure-time summer 118 and the downstream flow pressure-time summer 122. During an upstream flow segment, sampled data is numerically summed in a first summer 118 to provide an upstream flow pressure-time numerical integral sum. The upstream flow resistance is calculated by dividing the upstream flow pressure-time sum by the aspiration volume 106 in a first divider 120. The downstream flow resistance is similarly calculated by summing the sampled data in a second summer 122 and dividing the pressure-time sum by the infusion volume 106 in a second divider 124. Timing signals from the microprocessor 24 control which data the first and second summers 118 and 122 sum. In the case where the aspiration and infusion volumes are different, the volume block 106 would provide different volumes to the two respective dividers 120 and 124. Additionally, where different volumes are used for aspiration and infusion, the following equation may be used:

$$R_d = \frac{\sum_{k=0}^{M-1} P_{REV}(kT) - P_{baseline}}{Q_{REV}} - \frac{\sum_{k=M}^{2M-1} P_{FWD}(kT) - P_{baseline}}{Q_{FWD}}$$

At the conclusion of the hydraulic pressure response, the differential $R_d$ between the reverse flow resistance from the first divider 120 and the forward flow resistance from the second divider 124 is calculated in a comparator 126. The result $R_d$ is averaged by a second averager 110 as in the embodiment presented by FIG. 4 to calculate $R_d$ $_{AVG}$ to avoid artifacts such as those caused by patient motion. $R_d$ $_{AVG}$ is compared to a negative threshold value by comparator 114 and an alarm 116 issued if appropriate.

Figure 7:
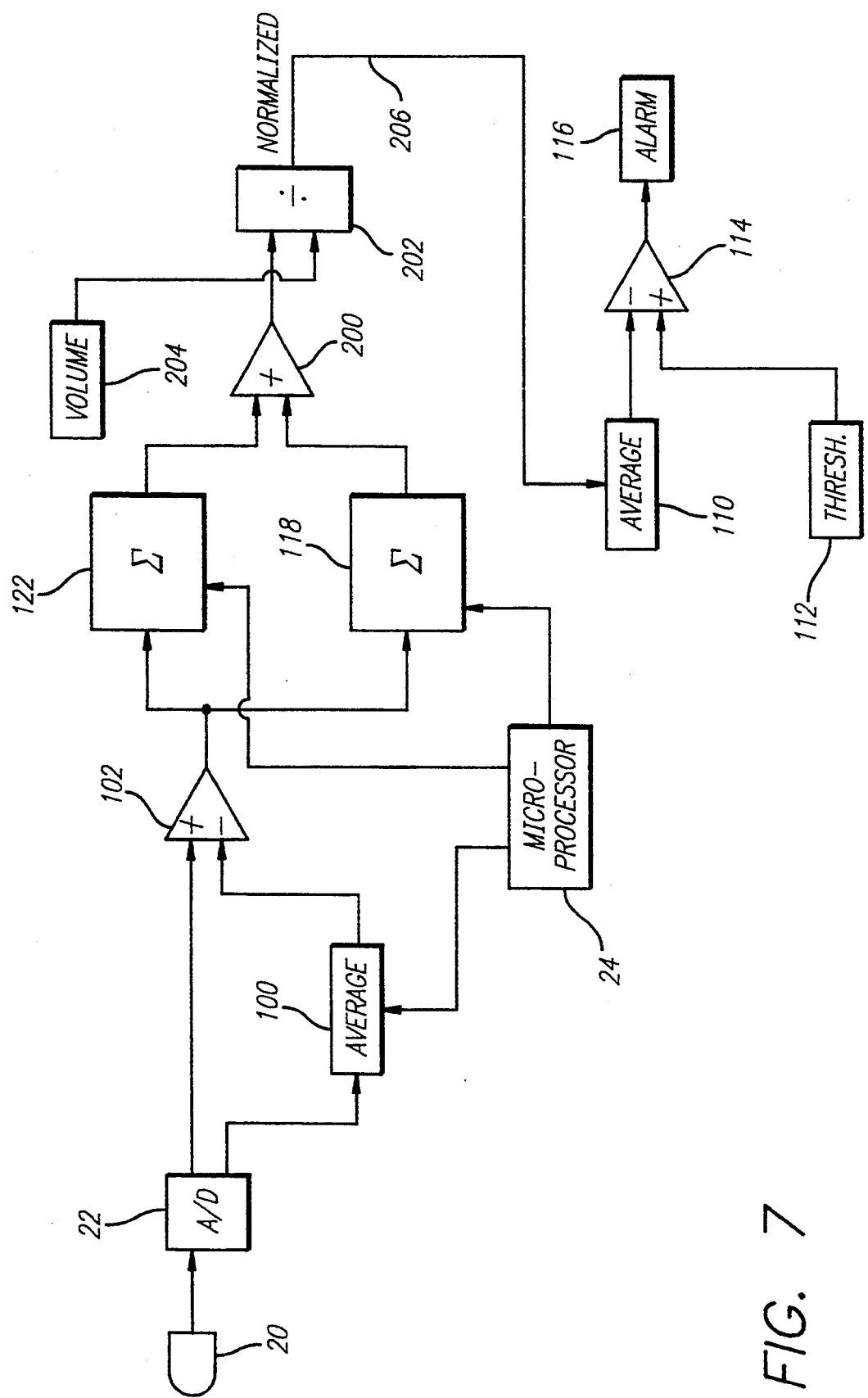
FIG. 7 presents an alternate system for determining cannula position in which the summed pressure-time responses are combined and the combined signal is normalized.

Referring now to FIG. 7, an alternate processing system is disclosed. The system is identical to that shown in FIG. 6 through the upstream flow pressure-time summer 118 and the downstream flow pressure-time summer 122. After these summers, the outputs are combined 200 and that combined signal is divided 202 by the volume of flow 204 to result in a normalized signal 206. That normalized signal 206 is filtered 110 in this embodiment, and is compared 114 to a threshold or range 112. If the signal is outside the range, an alarm 116 is given.

Figure 8A:
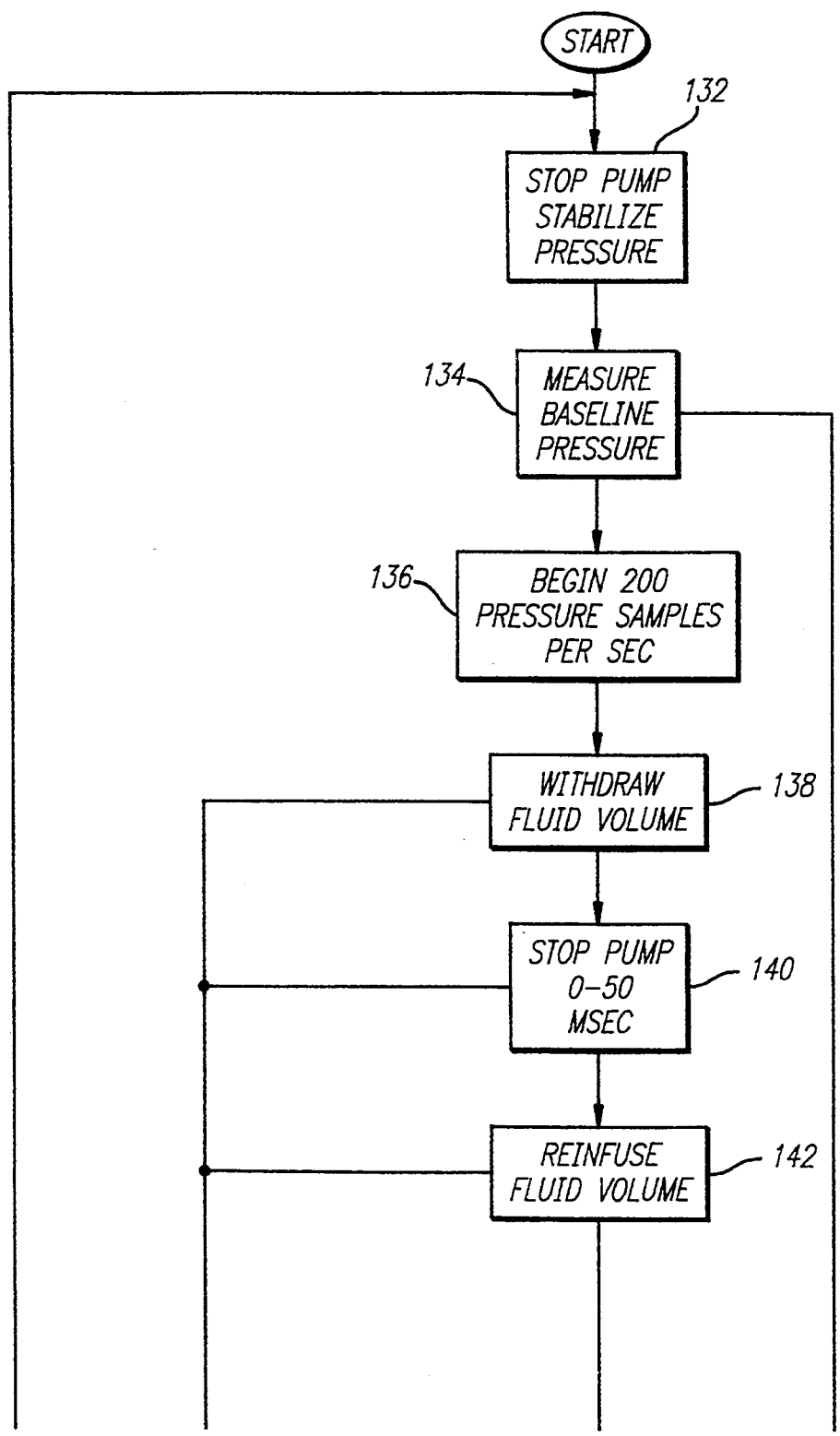
FIG. 8 is a flow diagram illustrating a method of determining cannula position in accordance with the invention where averaging of resistance differential is used.
Figure 8B:
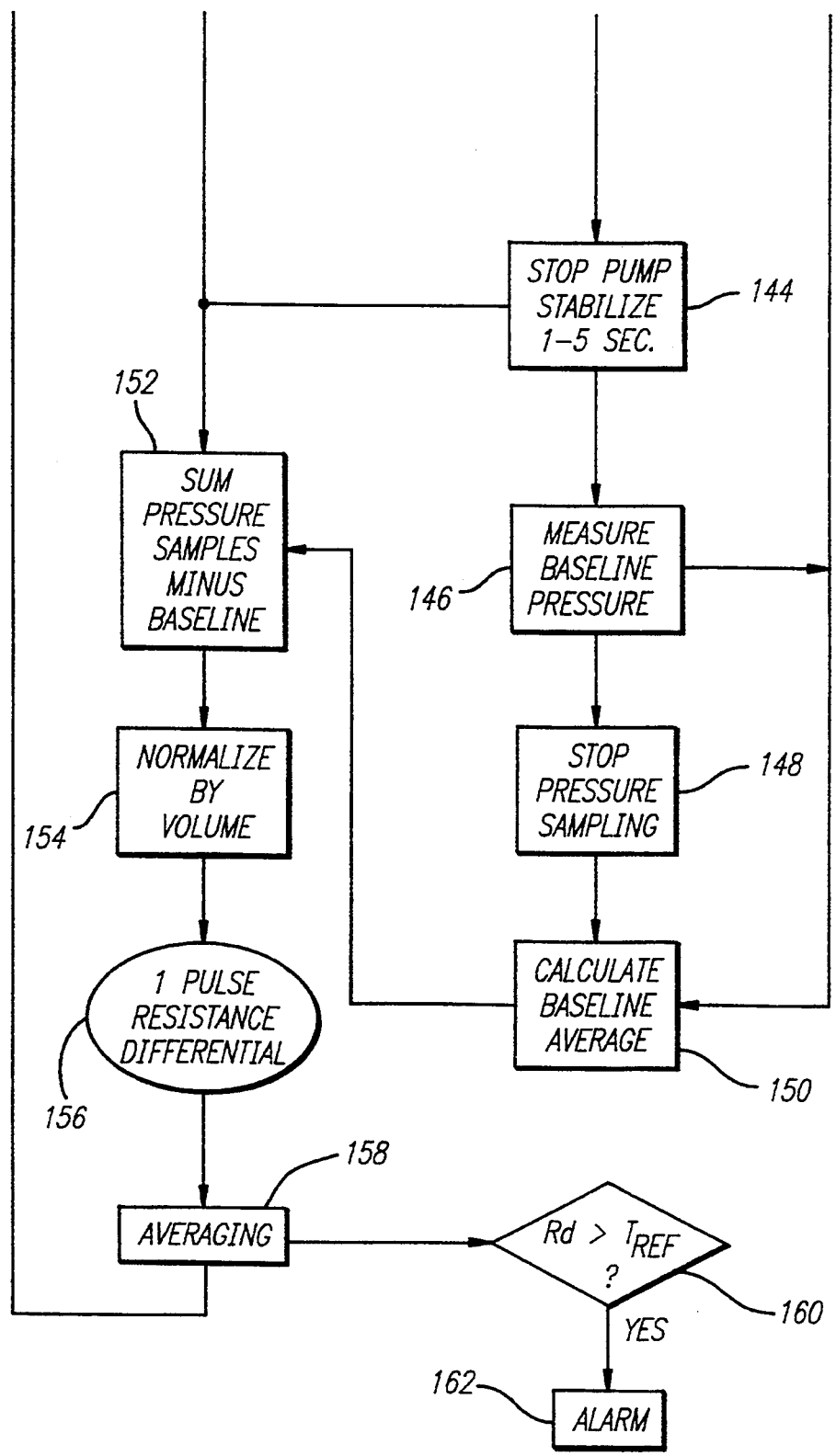

Referring now to FIG. 8 in which is illustrated the preferred form of an embodiment 130 of the method of the invention, the infusion pump is stopped 132 for approximately one to five seconds to stop the normal flow of intravenous fluid to the patient to substantially eliminate the flow induced pressure variations in the fluid administration system. The first measurement of the stabilized pressure baseline is then taken 134 and the continuous measurement 136 of IV fluid pressure is initiated at the rate of typically 200 samples per second. While the fluid pressure is thus being monitored, a relatively small precise volume of fluid is aspirated in step 138 in an upstream flow volume in a relatively short period of time, typically from 3 to 30 milliseconds. The volume of fluid withdrawn is precisely determined, but may typically range from 1 to 12 microliters. The volume of 1 to 12 microliters is typically considered to be so small as to result in minimal hemodynamic or injurious effects if the cannula is accidentally positioned in the interstitial space or against the vessel wall. The preferred pump for achieving this precise withdrawal of a volume of fluid is a linear peristaltic type of pump, which can provide a steady flow rate and the bidirectional patterns.

Following aspiration of the fluid, the pump may be stopped at step 140 for a period of up to 50 milliseconds in order to allow the dynamic system pressure response to the aspiration of the fluid to be fully developed, and in order to permit discrimination of forward flow resistance from reverse flow resistance. The same volume of fluid is then reinfused at step 142 in a downstream flow volume. In practice, the rate of reinfusion can be different from the rate of aspiration. At step 144, the pump is again stopped, typically for from one to five seconds in order to allow time for stabilization of pressure, after which the stabilized baseline pressure is again measured at step 146. The continuous pressure sampling is then stopped in step 148 while the normal infusion flow rate is resumed. A stabilized pressure baseline average is determined in step 150 as the numerical average of the stabilized pressure measurements taken before fluid withdrawal in step 138 and after fluid reinfusion in step 142. The numerical sum of the difference between the individual continuous pressure samples, measured during aspiration and reinfusion of fluid, and the calculated pressure baseline is then determined in step 152 and normalized in step 154 by the precise aspiration/reinfusion volume.

The resultant value in step 156 represents the net sum as a resistance differential which is preferably averaged at step 158 over a plurality of successive measurements, using sliding average, finite impulse response filtering, infinite impulse response filtering, least squares fit, or other such data averaging methods. The resultant overall average resistance differential will thus be relatively insensitive to abrupt changes in signals from the pressure transducer caused by patient motion or other momentary artifacts in the system. The average resistance differential $R_{d\ AVG}$ is then preferably compared in step 160 with a fixed negative threshold value $T_{REF}$ by the microprocessor. A small resistance differential occurs with a free flowing, unobstructed cannula. Some resistance exists due to the viscosity of blood being greater than the IV fluid. Increasing negative values represent a higher reverse flow resistance encountered during the brief aspiration period, followed by a lower forward resistance to flow during the reinfusion period. This type of response is typical of a cannula positioned near or against the surface of vascular tissue. When the averaged resistance differential $R_{d\ AVG}$ falls below the negative threshold value $T_{REF}$, the microprocessor preferably will trigger an alarm reaction at step 162 which can also involve shutdown of the fluid infusion system. The microprocessor may also override the operator input instructions to the flow rate controller 30 to cease fluid infusion in order to prevent injury to the patient.

Figure 9:
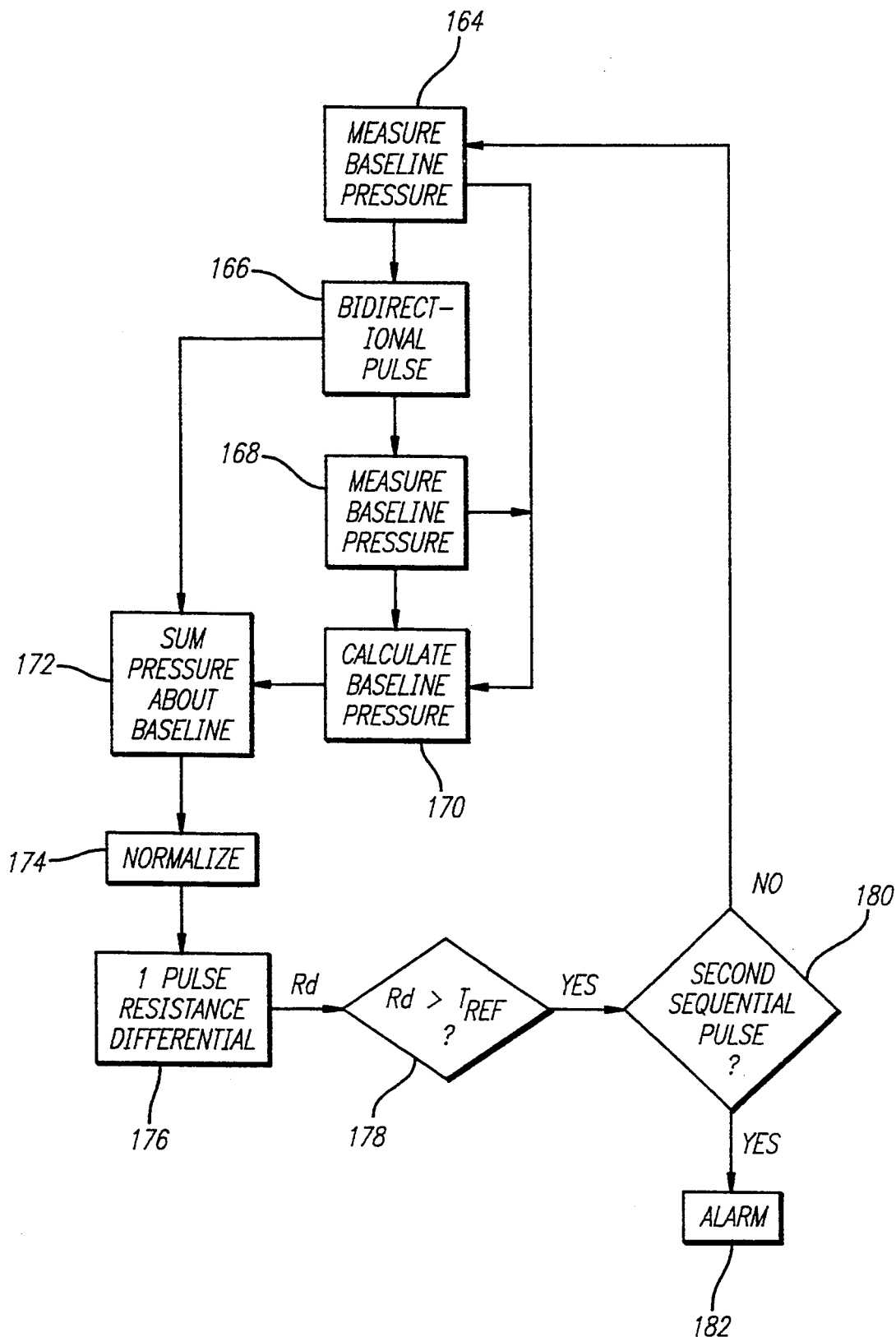
FIG. 9 is a flow diagram illustrating a method of determining cannula position wherein individual resistance differentials are considered and if outside an acceptable range, a second resistance differential is considered before an alarm is provided.

In another embodiment shown in FIG. 9, the system determines an alarm status on a pattern-by-pattern basis. As in FIG. 8, the baseline pressure is measured 164 in a non-flow period, the bidirectional flow pattern is applied 166, and the baseline pressure is measured in a second non-flow period 168. The baseline pressure is calculated 170 from the two baseline pressure periods. The pressure response to the bidirectional flow pattern is summed about the baseline pressure 172 and the result normalized 174. This results in a one-pattern resistance differential $R_d$ 176. This $R_d$ is compared to a negative threshold value $T_{REF}$ 178 and if less, the processor determines if this is the second flow pattern in sequence which has been less than $T_{REF}$. If not, the process is repeated by returning to measuring baseline pressure 164. If this is the second sequential flow pattern to be less than $T_{REF}$, an alarm is declared 182.

Although a pump has been disclosed above as providing the control over the fluid system to cause the bidirectional flow patterns, the fluid withdrawal and reinfusion flow volumes can also be generated by other methods, such as by displacement of the side wall of a flexible IV tube by an electrically controlled solenoid or similar electromechanical actuators. In a quiescent stage, the tubing would be slightly compressed by the actuator, and upstream flow would be developed by moving the actuator away from the tube. Downstream flow would then be developed by a return to the quiescent position.

Additionally, FIGS. 7 and 8 illustrate that the baseline pressure is measured each time before and after the bidirectional flow patterns. Other arrangements are possible, such as where the baseline pressure is measured only before the bidirectional flow pattern, or only before or after every second bidirectional flow pattern. Also, the determination of an alarm was explained as the resistance differential being less than a negative threshold $T_{REF}$. In one embodiment, the alarm is provided if the $R_d$ or $R_{d\ AVG}$ is outside a range. The range in this case would be all positive values and all negative values which are greater than $T_{REF}$. For example, where $T_{REF}$ is $-3.0$ volts, the acceptable range is all voltage values above $-3.0$ volts. To be outside the range, the value must be less than $-3.0$ volts.

In another embodiment, the volume reinfused may differ from the volume aspirated during the bidirectional flow pattern. This would result in a non-zero net quantity during the flow pattern; however, the two different quantities can both be kept small enough so as to not have any clinical effects. In some cases, the use of a larger volume for infusion than that used for aspiration may have the beneficial effect of flushing out any blood remaining in the administration set after aspiration.

In another embodiment, the volume of aspiration and reinfusion may be moved in the administration set line in a shorter time period to lessen the opportunity for external effects such as breathing or movement to have an impact on the position determination.

In view of the foregoing, it has been demonstrated that the method of the present invention offers the advantages of utilizing a relatively small volume of fluid in a relatively short period of time, to create a zero net volume bidirectional flow pattern having a withdrawal phase and reinfusion phase, minimizing potential vascular damage even in a particularly dangerous situation in which a cannula is positioned against a vessel wall. The utilization of the bidirectional flow pattern is also unique in forming a momentary but nondamaging seal against the vessel wall to create a readily detectable large negative pressure transient. The summation process is particularly useful in extracting a single value representative of the differential of the pressure-time sum developed during the bidirectional pressure patterns, and the use of the normalization step allows direct comparison of bidirectional flow patterns using varying aspiration volumes. The use of statistical methods averaging more than one individual resistance differential reading makes the method of the invention relatively immune to spurious conditions and noise.

Although specific embodiments of the invention have been described and illustrated, it is clear that it is susceptible to numerous modifications and adaptations within the ability of those skilled in the art and without the exercise of inventive faculty. Thus, it should be understood that various changes in form, detail and use of the present invention may be made without departing from the spirit and scope of the invention.

What is claimed is:

1. A method for determining the position of a cannula inserted into the vascular system of a patient, the cannula coupled to the downstream end of a conduit that is connected at its upstream end to a reservoir of fluid, the method comprising the steps of:
   a. establishing a baseline pressure based on the pressure in the conduit when no flow of fluid is occurring;
   b. moving a first predetermined quantity of fluid towards the upstream end of the conduit;
   c. measuring the pressure in the conduit during the step of moving the predetermined quantity of fluid towards the upstream end;
   d. moving a second predetermined quantity of fluid towards the downstream end of the conduit;
   e. measuring the pressure in the conduit during the step of moving the predetermined quantity of fluid towards the downstream end;
   f. summing the differences between the measured pressures and the baseline pressure;
   g. normalizing the pressure difference sum by the predetermined quantity of fluid;
   h. comparing the normalized sum to a predetermined range; and
   i. providing an alarm if the normalized sum is outside the predetermined range
   j. wherein steps (a), (f), (g), (h), and (i) are performed by a processor.

2. The method of claim 1 wherein the step of establishing the baseline pressure comprises the steps of:
   establishing a downstream delivery flow of the fluid through the conduit into the patient;
   stopping the delivery flow through the conduit for a first predetermined time period before the step of moving the predetermined quantity of fluid towards the upstream end;
   measuring the pressure during the first predetermined time period;
   stopping the delivery flow through the conduit for a second predetermined time period after the step of moving the predetermined quantity of fluid towards the downstream end;
   measuring the pressure during the second predetermined time period; and
   determining the baseline pressure by the processor by taking the average of the pressures during the first and second predetermined time periods.

3. The method of claim 1 further comprising the steps of:
   repeating steps a. through g. at least once;
   by the processor filtering the normalized pressure difference sums over the number of times steps a. through g. were repeated to provide a filtered normalized sum;
   conducting step h. on the filtered normalized sums; and
   wherein step i provides the alarm only if the filtered normalized sum is outside the predetermined range.

4. The method of claim 3 wherein the step of filtering by the processor comprises one of the steps selected from the group consisting of:
   averaging the normalized pressure difference sums;
   taking a sliding average of the normalized pressure difference sums;
   filtering the normalized pressure difference sum with a finite impulse response filter;
   filtering the normalized pressure difference sum with an infinite impulse response filter; and
   taking a least squares fit of the normalized pressure difference sums.

5. The method of claim 1 further comprising the step of stopping the normal flow through the conduit for a selected time period between the steps of moving the predetermined quantity of fluid towards the upstream end and the step of moving the predetermined quantity of fluid towards the downstream end of the conduit.

6. The method of claim 5 wherein the step of stopping the flow for a selected time period comprises the step of selecting the time period to be long enough for the pressure in the conduit to stabilize.

7. The method of claim 1 wherein the step of providing an alarm by the processor comprises the steps of:
   repeating steps a. through h. again if the normalized sum is outside the predetermined range; and
   providing an alarm only if after steps a. through h. have been repeated, the normalized sum remains outside the predetermined range.

8. The method of claim 1 wherein the step of summing by the processor comprises the steps of:
   computing the sum of the difference between the measured pressure during the upstream flow of the predetermined quantity of fluid and the baseline pressure;
   computing the sum of the difference between the measured pressure during the downstream flow of the predetermined quantity and the baseline pressure; and
   summing the computed sums.

9. The method of claim 1 further comprising the step of applying a pump to the conduit to perform the steps of moving the predetermined quantity of fluid, the pump being adapted for occluding the conduit at all times; and
   wherein the steps of measuring the pressure in the conduit comprise measuring the pressure in the conduit at a point between the cannula and the point of occlusion provided by the pump.

10. The method of claim 9 comprising the steps of:
    stopping the pump for a first time period and measuring the pressure in the conduit during this time period;
    pumping the predetermined quantity of fluid towards the upstream end of the conduit in a second time period which occurs after the first time period;
    stopping the pump for a third time period to establish a predetermined pressure level, the third time period occurring after the second;
    pumping the predetermined quantity of fluid towards the downstream end of the conduit in a fourth time period, the fourth period following the third period;
    stopping the pump for a fifth time period and measuring the pressure in the conduit during this time period, the fifth period occurring after the fourth period;
    wherein the step of establishing the baseline pressure by the processor comprises the step of averaging the pressures measured during the first and fifth time periods; and the step of summing comprises summing by the processor the pressures measured during the second and fourth time periods.

11. The method of claim 1 wherein the first and second predetermined quantities of fluid are equal.

12. A method for determining the position of a cannula inserted into the vascular system of a patient, the cannula coupled to the downstream end of a conduit that is connected at its upstream end to a reservoir of fluid, the method comprising the steps of:
   a. moving a predetermined quantity of fluid towards the upstream end of the conduit;
   b. measuring the pressure in the conduit during the step of moving the predetermined quantity of fluid towards the upstream end;
   c. moving the predetermined quantity of fluid towards the downstream end of the conduit;
   d. measuring the pressure in the conduit during the step of moving the predetermined quantity of fluid towards the downstream end;
   e. computing the reverse resistance to the movement of the quantity of fluid towards the upstream end of the conduit based on the pressure measured during the step of moving the predetermined quantity of fluid towards the upstream end;
   f. computing the forward resistance to the movement of the quantity of fluid towards the downstream end based on the step of moving the predetermined quantity of fluid towards the downstream end;
   g. taking the difference between the forward resistance and the reverse resistance; and
   h. providing an alarm if the resistance difference is outside a predetermined range
   j. wherein steps (e), (f), (g), and (h) are performed by a processor.

13. The method of claim 12 further comprising the step of establishing a baseline pressure by the processor based on the pressure in the conduit when no flow is occurring through the conduit; and
   wherein the steps of computing by the processor include summing the measured pressures about the baseline pressure.

14. The method of claim 13 wherein the step of establishing the baseline pressure by the processor comprises the steps of:
   establishing a downstream delivery flow of the fluid through the conduit into the patient;
   stopping the delivery flow through the conduit for a first predetermined time period before the step of moving the first predetermined quantity of fluid towards the upstream end of the conduit;
   measuring the pressure during the first predetermined time period;
   stopping the delivery flow through the conduit for a second predetermined time period after the step of moving the second predetermined quantity of fluid towards the downstream end;
   measuring the pressure during the second predetermined time period; and
   determining the baseline pressure by taking the average of the pressures during the first and second predetermined time periods.

15. The method of claim 12 further comprising: repeating steps a. through g. at least once;
   filtering the resistance differences by the processor over the number of times steps a. through g. were repeated to provide a filtered resistance difference; and
   conducting step h. only on the filtered resistance difference.

16. The method of claim 15 wherein the step of filtering by the processor comprises the step of averaging the resistance differences.

17. The method of claim 15 wherein the step of providing an alarm by the processor comprises the steps of:
   repeating steps a. through g. again if the filtered resistance difference is outside the predetermined range; and
   providing an alarm only if after the steps having been repeated, the filtered resistance difference remains outside the range.

18. The method of claim 12 further comprising the step of stopping the normal flow through the conduit for a selected time period between the steps of moving the predetermined quantity of fluid towards the upstream end of the conduit and the step of moving the predetermined quantity of fluid towards the downstream end of the conduit.

19. The method of claim 18 wherein the step of stopping the flow for a selected time period comprises the step of selecting the time period to be long enough for the pressure in the conduit to stabilize.

20. The method of claim 12 further comprising the step of applying a pump to the conduit to perform the steps of moving the predetermined quantity of fluid, the pump being adapted for occluding the conduit at all times; and
   wherein the steps of measuring the pressure in the conduit comprise measuring the pressure at a conduit location between the cannula and the point of occlusion provided by the pump.

21. The method of claim 20 further comprising the steps of:
   stopping the pump for a first time period and measuring the pressure in the conduit during this time period;
   pumping the predetermined quantity of fluid towards the upstream end of the conduit in a second time period which occurs after the first time period;
   stopping the pump for a third time period to establish a predetermined pressure level, the third time period occurring after the second;
   pumping the predetermined quantity of fluid towards the downstream end of the conduit in a fourth time period, the fourth period following the third period;
   stopping the pump for a fifth time period and measuring the pressure in the conduit during this time period, the fifth period occurring after the fourth period;
   wherein the step of computing the reverse resistance by the processor includes basing the computation on the pressure sensed during the second time period; and
   wherein the step of computing the forward resistance by the processor includes basing the computation on the pressure sensed during the fourth time period.

22. The method of claim 21 further comprising the step of establishing a baseline pressure by the processor based on the pressure in the conduit during the first and fifth time periods; and
   wherein the steps of computing by the processor include summing the measured pressures about the baseline pressure.

23. A system for determining the position of a cannula inserted into the vascular system of a patient, the cannula coupled to the downstream end of a conduit that is connected at its upstream end to a reservoir of fluid and a flow control device engaged with the conduit to control the flow of fluid through the conduit, the flow control device occluding the conduit continuously, the system comprising:

a pressure sensor for communication with the fluid in the conduit downstream of the occlusion provided by the flow control device, the pressure sensor for providing a pressure signal representative of the pressure of the fluid;

a processor for:
receiving the pressure signal provided by the pressure sensor;
controlling the flow control device to stop flow in the conduit and establish a baseline pressure based on the pressure signal received from the pressure sensor during this period of stopped flow;
controlling the flow control device to move a first predetermined quantity of fluid in the conduit in an upstream direction and a second predetermined quantity of fluid in a downstream direction;
summing the differences between the pressure signals received from the pressure sensor during the upstream and the downstream flows of the predetermined quantity of fluid and the baseline pressure;
normalizing the pressure difference sum by the predetermined quantity of fluid; and
providing an alarm if the normalized sum is outside a predetermined range.

24. The system of claim 23 wherein the processor is further connected to:
control the flow control device to stop flow through the conduit before and after it has moved the predetermined quantity of fluid in an upstream direction and in a downstream direction;
receive the pressure signals provided by the pressure sensor during these periods of stopped flow; and
determine the baseline pressure by averaging the pressure signals received during the periods of stopped flow.

25. The system of claim 23 wherein the processor is connected to:
control the flow control device to move the predetermined quantity of fluid in the conduit in an upstream direction and in a downstream direction multiple times;
sum the differences between the baseline pressure and the pressure signals received from the pressure sensor during the upstream flow and the downstream flow for each repetition;
normalize each pressure difference sum by the predetermined quantity of fluid for each repetition;
filter the normalized pressure difference sums over the number of multiple times to provide a filtered normalized sum; and
provide the alarm only if the filtered normalized sum is outside the predetermined range.

26. The system of claim 25 wherein the processor is further connected to determine the average of the normalized pressure difference sums as the filtered normalized sum.

27. The system of claim 23 wherein the processor is further connected to stop the flow of fluid through the conduit for a first selected time period between the period of moving the predetermined quantity of fluid towards the upstream end and the period of moving the predetermined quantity of fluid towards the downstream end of the conduit.

28. The system of claim 27 wherein the processor selects the first time period to be long enough for the pressure in the conduit to stabilize.

29. The system of claim 23 wherein the processor is further connected to:
control the flow control device to repeat the movements of the predetermined quantity of fluid in the conduit in the upstream direction and in the downstream direction for at least one additional time if the normalized sum is outside the predetermined range;
sum the differences for each repetition between the baseline pressure and the pressure signals received from the pressure sensor during the upstream and the downstream flows;
normalize each pressure difference sum by the predetermined quantity of fluid for each respective repetition; and.
provide the alarm only if the normalized sum of one or more repetitions remains outside the predetermined range.

30. The system of claim 23 wherein as part of the sum of the differences, the processor is further connected to:
compute the sum of the difference between the measured pressure during the upstream flow of the predetermined quantity of fluid and the baseline pressure;
compute the sum of the difference between the measured pressure during the downstream flow of the predetermined quantity and the baseline pressure; and
sum the computed sums.

31. The system of claim 23 wherein the processor is further connected to:
stop the flow control device for a first time period and measure the pressure in the conduit during this time period;
pump the first predetermined quantity of fluid towards the upstream end of the conduit in a second time period which occurs after the first time period;
stop the flow control device for a third time period to establish a predetermined pressure level, the third time period occurring after the second;
pump the second predetermined quantity of fluid towards the downstream end of the conduit in a fourth time period, the fourth period following the third period;
stop the flow control device for a fifth time period and measure the pressure in the conduit during this time period, the fifth period occurring after the fourth period;
establish the baseline pressure by averaging the pressures measured during the first and fifth time periods; and
sum the differences between the pressure signals measured during the second and fourth time periods and the baseline pressure.

32. The system of claim 23 wherein the first and second predetermined quantities of fluid are equal.

33. A system for determining the position of a cannula inserted into the vascular system of a patient, the cannula coupled to the downstream end of a conduit that is connected at its upstream end to a reservoir of fluid and a flow control device engaged with the conduit to control the flow of fluid through the conduit, the flow control device occluding the conduit continuously, the system comprising:

a pressure sensor for communication with the fluid in the conduit downstream of the occlusion provided by the flow control device, the pressure sensor for providing a pressure signal representative of the pressure of the fluid;

a processor for:

receiving the pressure signal provided by the pressure sensor;

controlling the flow control device to move a predetermined quantity of fluid in the conduit in an upstream direction and in a downstream direction;

computing the reverse resistance to the movement of the quantity of fluid towards the upstream end of the conduit based on the pressure signal received during the movement;

computing the forward resistance to the movement of the quantity of fluid towards the downstream end of the conduit based on the pressure signals received during the movement;

determining the difference between the forward resistance and the reverse resistance; and providing an alarm if the resistance difference is outside a predetermined range.

34. The system of claim 33 wherein the processor is further connected to:

establish a baseline pressure based on the pressure in the conduit when no flow of fluid is occurring through the conduit; and numerically sum the measured pressures about the baseline pressure when computing the resistances.

35. The system of claim 34 wherein the processor is further connected to:

establish a downstream delivery flow of the fluid through the conduit into the patient;

stop the delivery flow through the conduit for a first predetermined time period before moving the predetermined quantity of fluid towards the upstream end of the conduit;

measure the pressure during the first predetermined time period;

stop the delivery flow through the conduit for a second predetermined time period after moving the predetermined quantity of fluid towards the downstream end;

measure the pressure during the second predetermined time period; and determine the baseline pressure by averaging the pressures during the first and second predetermined time periods.

36. The system of claim 34 wherein the processor is further connected to:

stop the flow control device for a first time period and measure the pressure in the conduit during this time period;

pump the predetermined quantity of fluid towards the upstream end of the conduit in a second time period which occurs after the first time period;

stop the flow control device for a third time period to establish a predetermined pressure level, the third time period occurring after the second;

pump the predetermined quantity of fluid towards the downstream end of the conduit in a fourth time period, the fourth period following the third period;

stop the flow control device for a fifth time period and measure the pressure in the conduit during this time period, the fifth period occurring after the fourth period;

establish the baseline pressure based on the pressures measured during the first and fifth time periods;

compute the reverse resistance based on the pressure sensed during the second time period; and compute the forward resistance based on the pressure sensed during the fourth time period.

37. The system of claim 33 wherein the processor is further connected to:

repeat the movement of the predetermined quantity of fluid in the upstream and downstream directions at least once;

filter the resistance differences over the number of repetitions to provide a filtered resistance difference;

compute the reverse and forward resistances for each repetition;

determine the resistance difference for each repetition; and provide the alarm only if the filtered resistance difference is outside the predetermined range.

38. The system of claim 37 wherein the processor is further connected to determine the average of the resistance differences as the filtered resistance difference.

39. The system of claim 33 wherein the processor is further connected to:

control the flow control device to repeat the movements of the predetermined quantity of fluid in the conduit in the upstream direction and in the downstream direction for at least one additional time if the resistance difference is outside the predetermined range;

compute the reverse and forward resistances for each repetition;

determine the resistance difference for each repetition; and provide the alarm only if the resistance difference of one or more repetitions remains outside the predetermined range.

40. The system of claim 33 wherein the processor is further connected to stop the flow through the conduit for a first selected time period between moving the predetermined quantity of fluid towards the upstream end of the conduit and moving the predetermined quantity of fluid towards the downstream end of the conduit.

41. The system of claim 40 wherein the processor selects the first time period to be long enough for the pressure in the conduit to stabilize.

* * * * *